US005630412A

United States Patent [19]

Dubruille et al.

[11] Patent Number: 5,630,412

[45] Date of Patent: May 20, 1997

[54] PROTECTIVE EQUIPMENT FOR THE HEAD COMPRISING A BREATHING MASK AND AN OPTICAL SCREEN

[75] Inventors: Alain Dubruille, Rambouillet; Frédéric Berthet, Maurepas, both of France

[73] Assignee: Intertechnique, Plaisir, France

[21] Appl. No.: 530,191

[22] PCT Filed: Feb. 2, 1995

[86] PCT No.: PCT/FR95/00134

§ 371 Date: Oct. 2, 1995

§ 102(e) Date: Oct. 2, 1995

[87] PCT Pub. No.: WO95/20995

PCT Pub. Date: Aug. 10, 1995

[30] Foreign Application Priority Data

Feb. 2, 1994 [FR] France .................................. 94 01159

[51] Int. Cl.$^{6}$ ............................ A62B 7/00; A61M 16/00

[52] U.S. Cl. ............................... 128/206.23; 128/206.21; 128/206.24; 128/206.25; 128/206.27; 128/206.28; 128/207.11; 128/201.22; 128/201.23; 2/421

[58] Field of Search ......................... 128/200.28, 201.12, 128/201.18, 201.22, 201.23, 201.24, 202.27, 204.27, 206.21, 206.23, 206.24, 206.25, 206.26, 206.27, 206.28, 207.11, 204.29, 201.25; 2/6, 421, 424, 9, 427

[56] References Cited

U.S. PATENT DOCUMENTS

| | | | |
|---|---|---|---|
| Re. 31,424 | 10/1983 | Ernsting et al. | 128/206.21 |
| 2,942,602 | 12/1960 | Seeler | 128/201.23 |
| 3,065,747 | 11/1962 | Forkel | 128/201.24 |
| 3,971,368 | 7/1976 | Forbes et al. | 128/206.27 |
| 4,110,847 | 9/1978 | Dera | 2/421 |
| 4,347,630 | 9/1982 | Arai et al. | 2/421 |
| 4,555,815 | 12/1985 | Walther | 2/424 |
| 4,648,138 | 3/1987 | Brigden et al. | 2/421 |
| 4,734,940 | 4/1988 | Galet et al. | 2/6.4 |
| 5,003,632 | 4/1991 | Claude | 2/6.5 |

*Primary Examiner*—Vincent Millin
*Assistant Examiner*—V. Srivastava
*Attorney, Agent, or Firm*—Larson and Taylor

[57] ABSTRACT

The protective equipment for the head comprises a breathing mask provided with a harness and connectable to a source of breathing gas, together with a screen (22) for protecting the eyes against smoke, the screen being provided with a peripheral sealing gasket (26) that presses against the face and against the mask. The mask and the screen are distinct and separable. Manually releasable locking means lock the screen to the mask and bear against the mask so as to press the gasket against the face. The equipment is particularly intended for use by aircraft flight crew members.

12 Claims, 3 Drawing Sheets

PROTECTIVE EQUIPMENT FOR THE HEAD COMPRISING A BREATHING MASK AND AN OPTICAL SCREEN

The present invention relates to protective equipment for the head of the type comprising a breathing mask provided with a harness and connectable to a source of breathings gas enabling the mask to be put under positive pressure relative to the atmosphere, and a screen for protecting the eyes against smoke, the screen being provided with a peripheral sealing gasket for pressing against the face and the mask, the screen and the mask being separate and distinct from each other.

Such protective equipment for the head of the type defined above is already known. The breathing mask, provided with a regulator, protects the wearer of the mask against lack of oxygen and against smoke or toxic gases penetrating into the respiratory tract. The harness serves to press the mask against the face with sufficient pressure to ensure sealing. When it is in place, the protective screen protects the eyes against smoke and irritating gases.

A major, but non-exclusive application of the invention lies in aviation. The mask is then designed in particular to provide protection against lack of oxygen in the event of pressurization being lost at high altitude, thus requiring the mask to be provided with a demand regulator for feeding gas at positive pressure as a function of altitude, and requiring the harness to be capable of pressing the mask against the face with sufficient force to prevent leaks appearing that would otherwise reduce the positive pressure inside the mask. To satisfy these conditions, the harness may be constituted by a strap that exerts a force which is adjustable either automatically (e.g. by modifying an internal pressure when the straps are extensible by inflation), or manually (e.g. when the harness includes not only pneumatically extensible straps, but also cloth straps that are loose while the mask is in the storage position and that can be tightened manually).

Mask-and-screen assemblies have already been proposed that comprise a single block (U.S. Pat. No. design 304 384), thereby presenting a solution that is satisfactory when the mask is designed to be installed only an emergency. That solution is often unacceptable in other cases, e.g. equipment for pilots and copilots of transport aircraft which are required by regulations to carry equipment for providing protection against lack of oxygen on a permanent basis under certain flying conditions, in particular at very high altitude or when only one pilot is present in the cockpit. Under such circumstances, the screen constitutes a hindrance and also gives rise to a feeling of claustrophobia.

The present invention seeks in particular to provide protective equipment for the head that satisfies practical requirements better than previously known equipment, in particular with respect to making it possible or at least more convenient to use the mask on its own and to install the screen quickly in the event of need, or else to use the regulator mask with the screen mounted in place and to enable the screen portion to be removed if the user so desires. To this end, the invention provides, in particular, equipment of the type defined above, characterized in that it includes means for locking the screen on the mask, which means are manually releasable, and bear against the mask so as to press the gasket against the face.

To prevent smoke or toxic gas or irritating gas being kept in contact with the eyes, and to prevent condensation forming on the screen, the screen is advantageously provided with means that automatically open an inlet to allow breathing gas inside the mask to pass into the screen when the screen has been put into place and locked in position. The positive pressure relative to the atmosphere (which is always necessary inside the mask, even at normal atmospheric pressure, in order to ensure that the same smoke or gases cannot gain access to the respiratory tract) then causes breathing gas to pass into the screen, thereby sweeping out any smoke or gas that may have been captured therein.

The harness may be a harness for fitting rapidly, and suitable for fitting to any size of head or helmet (such as those described in document EP-A-028839 and French patent application FR 9211342, for example); it may be alternatively be constituted by straps provided with buckles for tightening purposes, and that is particularly appropriate when there is no need for the harness to be put on rapidly.

The invention will be better understood on reading the following description of particular embodiments given as non-limiting examples. The description refers to the accompanying drawings, in which.

Figure 3:
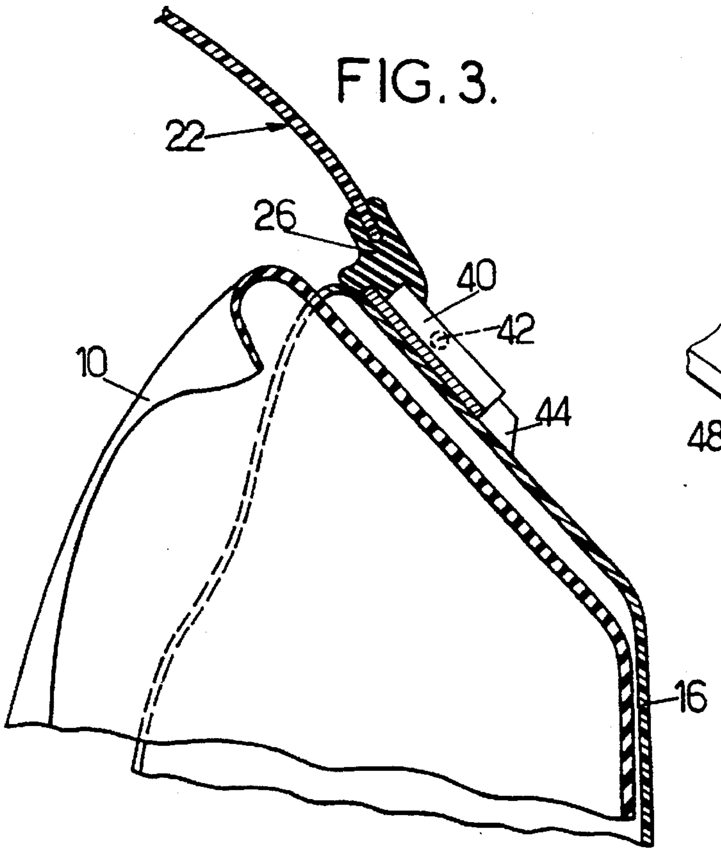
FIG. 3 is a section view showing one possible structure of the means for locking the screen on the mask.
Figure 4:
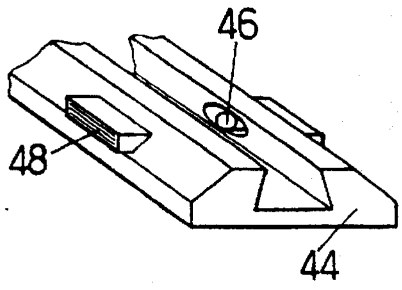
FIG. 4 is a detail perspective view showing the portion of the FIG. 3 locking means that is carried by the mask.
Figure 9:
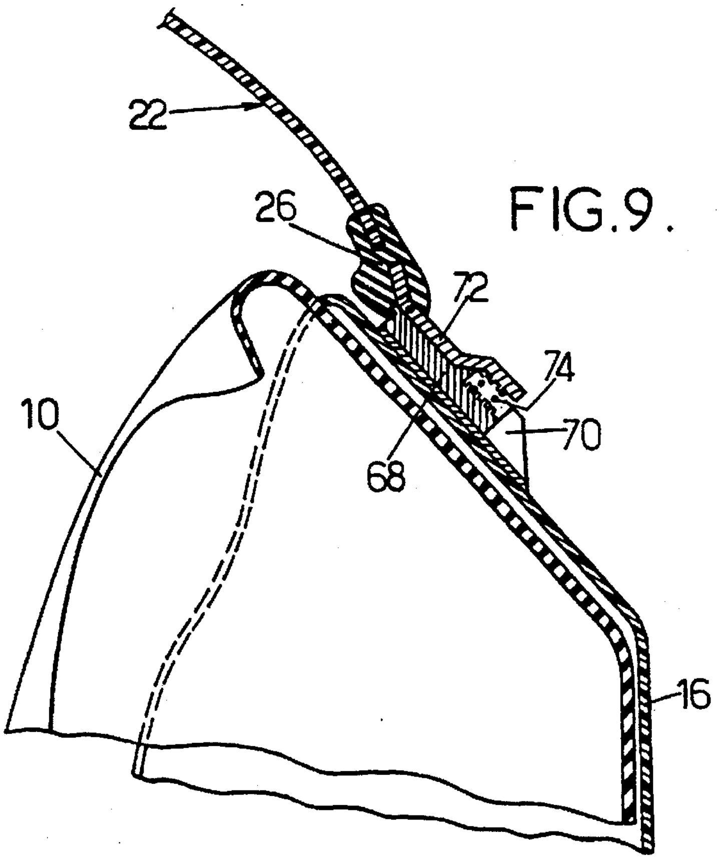
Figure 7:
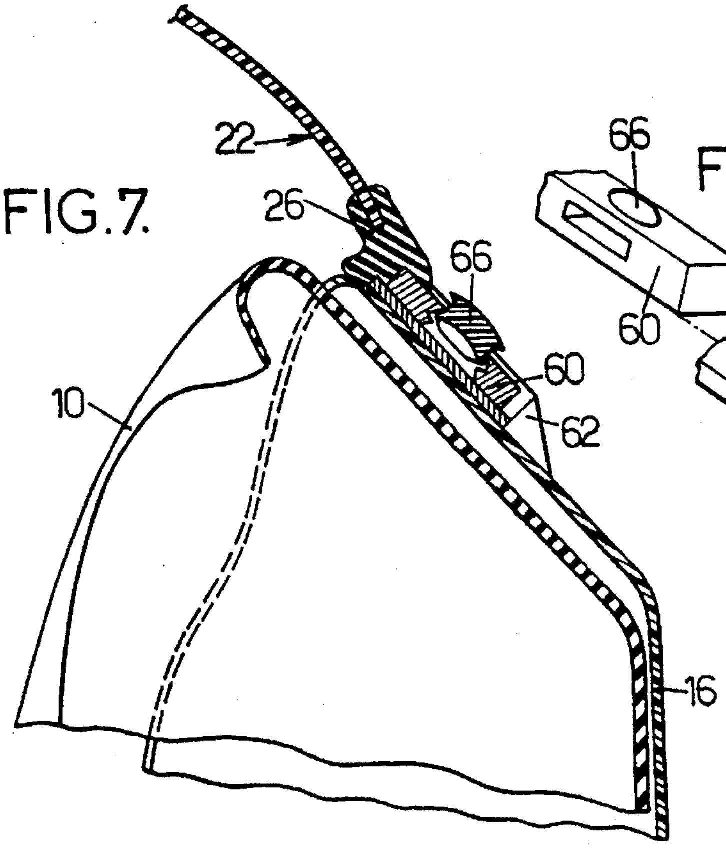
Figure 8:
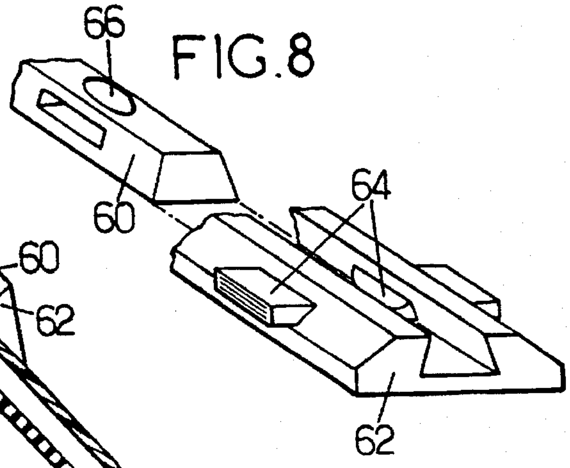

FIGS. 7 and 8, likewise similar to FIGS. 3 and 4, show yet another variant; and FIG. 9 is a diagrammatic section view showing means that enable the pressure with which the mask is applied against the face to be increased when screen locking is being put into place, so as to compensate for the additional lifting force due to the behavior of the face when the mask is used at positive relative pressure.

Figure 1:
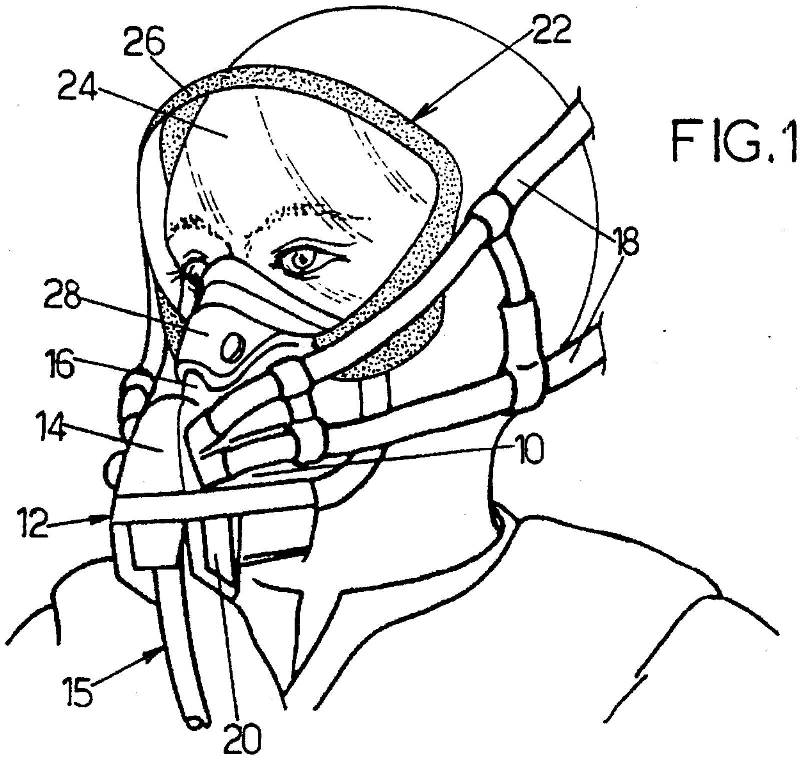
FIG. 1 shows the outside appearance of protective equipment constituting an embodiment of the invention, using a mask that is provided with a demand regulator and with a harness having inflatable straps.
Figure 2:
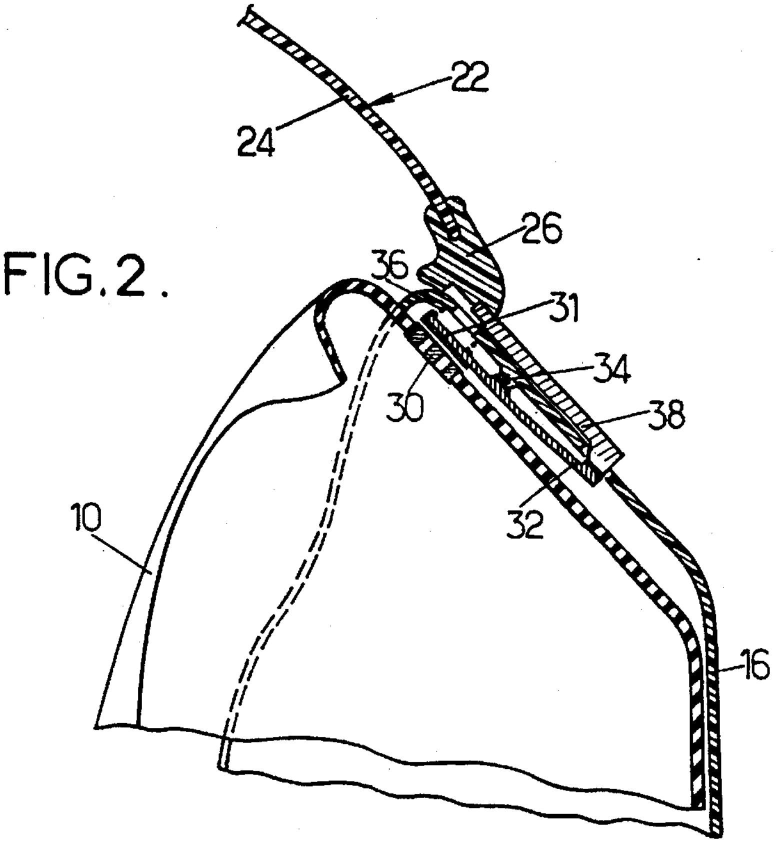
FIG. 2 is a fragmentary section through a portion of the mask and the screen, showing the means designed to provide communication between the inside of the mask and the inside of the screen when the screen is put into place.

The protective equipment shown diagrammatically in FIGS. 1 and 2 comprises a mask and a harness of generally known structure. For example, a description thereof may be found in document EP-A-0 288 391. The mask comprises a facepiece 10 that is fixed to a demand regulator 12 associated with a rigid connection block 14. The block 14 is secured to a shell 16 covering the front of the facepiece. The connection block 14 is designed to be connected to a source of breathing gas under pressure (generally oxygen under pressure) via a flexible hose 15. The harness shown by way of example has two straps 18 each constituted by an inner tube of resilient material contained within an inextensible sheet that puts a limit on elongation of the tube, said straps being connected to the block 14. The sheaths are of a length that enables the harness to be passed over heads of all sizes when both tubes are inflated by pressing on handles 20. The resilience of the tubes is sufficient to ensure suitable clamping on the head to enable the breathing equipment to be used when it is fed with gas under pressure.

The screen 22 includes a transparent window 24 of optical quality whose edges are held captive in a sealing gasket 26 and which is extended by a block 28 for fixing on the shell of the mask.

The top portion of the sealing gasket 26 that is designed to bear against the forehead and the temples may be of conventional structure. The bottom portion of the gasket which needs to bear against zones of the face and of the shell that include concave portions, is advantageously constituted in the form of a strip of foam material so as to achieve a large area of contact. In use, this bottom portion is received beneath the top strap 18. To make it easier to put the mask into place, the top strap can be moved away from the face in its zone close to its connection with the shell, e.g. by guiding it for a few centimeters over a length of rigid tube. In a variant embodiment, the bottom portion of the sealing gasket is wedge-shaped so as to lift the top strap when the screen is put into place on a mask that is already being worn by the user.

The screen 22 and the mask are advantageously designed in such a manner as to organize a flow of breathing gas inside the screen when the screen is in place. In particular, it is possible to admit breathing gas automatically or otherwise from the inside of the mask into the inside of the screen via means that are closed so long as the screen is not in place. The breathing gas may escape by leaking between the gasket and the skin. Slots may also be provided in the top portion of the gasket so as to guide the sweeping air.

By way of example, FIG. 2 shows breathing gas admission means comprising a valve suitable for placing in part on the top edge of the shell of the mask and in part on the gasket 10. This valve comprises a seat 30 pierced by holes and placed in the facepiece, and a closure lever 32 rotating on a pin 34 belonging to the shell. Sealing is provided by the gasket 31. A spring 36 urges the lever 32 towards the seat 30. The fixing block 28 belonging to the screen includes a tab 38 which, when the screen is in place, bears against one of the levers 32 in such a manner as to raise the other end away from the seat 30, thereby opening communication with the inside of the screen. Other structures would naturally be possible.

The fixing block 28 is designed to allow rapid installation on the shell 16 of the mask. The fixing means may be of very different structures, and only a few embodiments are given by way of example.

In the embodiment shown in FIGS. 3 and 4, the fixing block of the screen includes a slide 40 having balls 42 urged towards projecting positions by respective springs. The slide is designed to engage in a slideway 44 secured to the shell 16. Housings 46 are provided in the slideway to receive the balls and to lock the slide 40 automatically. Two pushers 48 are placed on either side of the slideway for pushing in the balls and for allowing the screen to be unlocked manually when it is no longer useful and can be removed. In a variant, the slideway is fixed to the screen and the slide to the shell.

Figure 5:
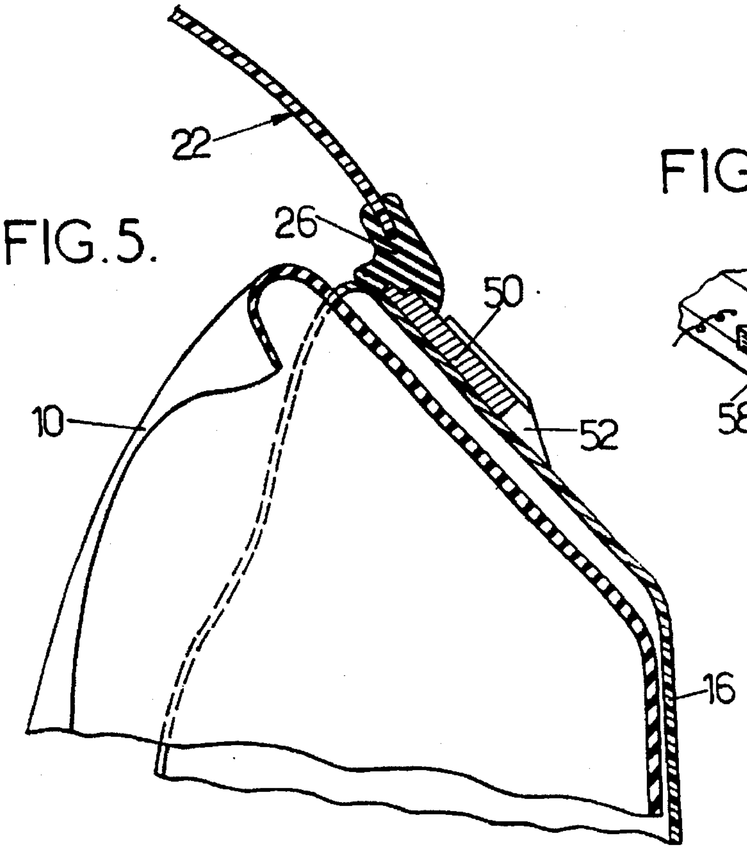
FIGS. 5 and 6 are similar to FIGS. 3 and 4 showing another embodiment of the locking means.
Figure 6:
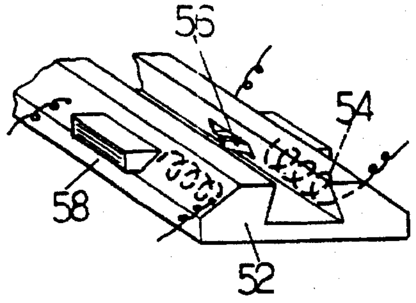

In the variant embodiment shown in FIGS. 5 and 6, a soft iron bar 50 is incorporated in the fixing block 28. This bar is designed to engage in a slideway 52 that is secured to the shell 16 and to be retained therein by an electromagnetic field created by coils 54 embodied in the slideway, whenever said coils are powered. The coil power supply is provided with means such as a tab 56 placed so as to be actuated by the bar 50 at the end of its insertion stroke. Unlocking can be performed by acting manually on a switch, using a pushbutton 58 similar to the pushbuttons 48 of FIG. 4.

It is also possible to provide retention by means of permanent magnets having an attractive force that is selected so as to hold the screen effectively while still leaving it possible to exert manual force to remove the mask against the action of the permanent magnets.

In the embodiment shown in FIGS. 7 and 8, the mask is locked manually after being put into place. The fixing block secured to the screen again includes a slide 60 which is designed to engage in a slideway 62 secured to the shell 16. Two manually-controlled latches 64 enable the slide to be locked in place once fully engaged, by being moved into engagement therewith under drive from the fingers of the user. Unlocking can then be achieved by using a button 66 that is held captive in the slide 60 and that is pushed into a projecting position as shown in FIG. 7 when the latches 64 are themselves pushed home. The user unlocks the screen by pressing on the button 66 which acts on sloping surfaces of the latches to move them apart from each other and to disengage them from the slide. In a variant embodiment, the latches 64 are urged towards each other by springs.

When the regulator mask (facepiece) is suitable for being fed at positive relative pressure, it is advantageous to provide a fixing block that increases the pressure with which the screen is pressed against the face. FIG. 9 shows means that can be provided for achieving this result.

In the example shown in FIG. 9, the fixing block includes a guide 68 designed to engage in a base 70 which may be integral with the slideway belonging to the mask fixing means. The guide is hinged behind a lever 72. A spring 74 is interposed between the other end of the lever and the guide 68.

In general, the screen does not have its own harness and the fixing block 28 is designed to press the sealing gasket 26 against the face with sufficient force in spite of the fact that the screen is cantilevered out relative to the mask. Nevertheless, it is also possible to provide a cloth strap on the harness. This strap is then relaxed or open except during periods of use so that it does not impede putting the screen into place.

In an aircraft, the equipment is generally stored in a box within reach of the pilot. When not in use, the mask is stored together with the screen locked thereon, so that in an emergency the pilot can place the mask-and-screen assembly on the face, can have breathing oxygen available in the locations specified by the regulations in force, and can be protected against smoke. If circumstances then do not require a screen to be worn, the pilot can take it off. To prevent the screen being forgotten, the storage box is advantageously designed in such a manner that the mask cannot be put back into place therein without the screen being fixed to the mask.

We claim:

1. A protective headgear comprising:

a breathing mask connectable to a source of breathable gas;

a harness for applying said breathing mask on a wearer's face; and a transparent eye shield for protecting the wearer's eyes against smoke, having peripheral sealing means arranged for being sealingly applied against the face and against said breathing mask;

said eye shield and breathing mask being separate and including mutually cooperating locking means for releasibly locking the eye shield onto the mask and forcibly applying said sealing means onto the face when locked.

2. Headgear according to claim 1, wherein said eye shield further includes means for providing a communication between an inside volume of the mask and an inside volume of the eye shield when they are locked together.

3. Headgear according to claim 1, wherein said communication means cmprise at least one valve having a valve seat placed on the mask in a location such as to open out inside the eye shield when the latter is locked on the breathing mask and means for forcibly opening said valve when the eye shield is being locked.

4. Headgear according to claim 1, wherein said eye shield and said mask carry means for causing a mechanical pressure with which the mask is applied to the face to increase while the eye shield is locked.

5. Headgear according to claim 4, wherein said eye shield screen is devoid of harness.

6. Headgear according to claim 1, wherein said locking means comprise only one slide fixed to one of the eye shield and a rigid shell of the mask, and one slideway fixed to the other of the rigid shell of the breathing mask and eye shield.

7. Headgear according to claim 6, wherein said locking means further include balls placed in the slide, means for urging them towards a laterally projecting position in which they engage recesses in the slideway, and pushout means carried by the slideway and manually actuatable for expelling said balls from said recessese.

8. Headgear according to claim 6, wherein said locking means include latches carried by said slideway and manually displaceable into a position where they engage the slide.

9. Headgear according to claim 6, wherein locking means include magnetic or electromagnetic means carried by said eye shield and said mask.

10. Headgear according to claim 1, wherein said harness is arrangec to provide a gap for insertion of a bottom portion of the sealing means between the face and a portion of the harness close to a connection thereof with the breathing mask.

11. A protective headgear according to claim 1, further comprising a storage box for said breathing mask, harness and eye shield, arranged for rendering it impossible to receive the mask and eye shield when they are separate.

12. A protective headgear comprising:

a breathing mask connectable to a source of breathable gas;

a harness for applying said breathing mask on a wearer's face; and a transparent eye shield devoid of harness, for protecting the wearer's eyes against smoke, having peripheral sealing means arranged for being sealingly applied against the face and against said breathing mask;

said eye shield and breathing mask being separate and including mutually cooperating locking means for releasibly locking the eye shield onto the mask and forcibly applying said sealing means onto the face when locked.

* * * * *